United States Patent
Yu et al.

(10) Patent No.: US 12,163,174 B1
(45) Date of Patent: Dec. 10, 2024

(54) METHOD FOR PRODUCING SCLAREOL BY FERMENTATION OF CIGAR TOBACCO FLOWER BUDS

(71) Applicants: Tobacco Research Institute of Hubei Province, Wuhan (CN); Hubei University of Technology, Wuhan (CN)

(72) Inventors: Jun Yu, Wuhan (CN); Chunlei Yang, Wuhan (CN); Zhi Wang, Wuhan (CN); Xiong Chen, Wuhan (CN); Zongping Li, Wuhan (CN); Jinpeng Yang, Wuhan (CN); Hao Li, Wuhan (CN); Lan Yao, Wuhan (CN); Xiongfei Rao, Wuhan (CN); Hao Peng, Wuhan (CN); Shiping Xu, Wuhan (CN); Wenming Wang, Wuhan (CN)

(73) Assignees: Tobacco Research Institute of Hubei Province, Wuhan (CN); Hubei University of Technology, Wuhan (CN)

( * ) Notice: Subject to any disclaimer, the term of this patent is extended or adjusted under 35 U.S.C. 154(b) by 0 days.

(21) Appl. No.: 18/661,739

(22) Filed: May 13, 2024

(30) Foreign Application Priority Data

May 26, 2023 (CN) .......................... 202310606790.7

(51) Int. Cl.
*C12P 7/02* (2006.01)
(52) U.S. Cl.
CPC ....................................... *C12P 7/02* (2013.01)
(58) Field of Classification Search
CPC ....................................................... C12P 7/02
See application file for complete search history.

(56) References Cited

FOREIGN PATENT DOCUMENTS

| | | |
|---|---|---|
| CN | 113355159 A | 9/2021 |
| JP | 2009060799 A | 3/2009 |

OTHER PUBLICATIONS

Ma et al., Engineering Sclareol Production on the Leaf Surface of Nicotiana tabacum. J. Agric. Food Chem., 2024, vol. 72: 13812-13823. (Year: 2024).*
Nanfen et al., Differential Analysis of Metabolomics of Cigar Tobacco Leaves of Different Varieties after Air-curing. Chinese Tobacco Sci., 2022, vol. 43(2): 77-85. (Year: 2022).*
Popova et al., GC-MS Composition and Olfactory Profile of Concretes from the Flowers of Four Nicotiana Species. Molecules, 2020, vol. 25, 2617, pp. 1-15. (Year: 2020).*
Vandamme et al., Bioflavours and fragrances via fermentation and biocatalysis. J. Chem. Technol. Biotechnol., 2022, vol. 77: 1323-1332. (Year: 2022).*
Xu et al., Optimization of fermentation treatment condition of tobacco bud and preparation of tobacco flavor. Hubei Agric. Sci., 2018, vol. 57(1): 100-111 (see provided English Machine Translation). (Year: 2018).*
Michel Schalk et al., Toward a Biosynthetic Route to Sclareol and Amber Odorants, Journal of the American Chemical Society, 2012, vol. 134, Issue 46, pp. 18900-18903.
Wei Yang et al., Engineering *Saccharomyces cerevisiae* for sclareol production, Chinese journal of biotechnology, 2013, vol. 29, Issue 8, pp. 1185-1192.
Yehua Song et al, High cell density culture of an engineered yeast strain for sclareol production, Chinese journal of biotechnology, 2015, vol. 31, Issue 1, pp. 147-151.
Zhang Xue et al,. Engineering *Saccharomyces cerevisiae* for Production of Limonene and Perillyl Alcohol, Tianjin University Thesis, 2021, full text.
Xu Chunping et al., Optimization of Fermentation Treatment Condition of Tobacco Bud and Preparation of Tobacco Flavor, Hubei Agricultural Sciences 2018, vol. 57, No. 1, pp. 100-111.

\* cited by examiner

*Primary Examiner* — Ganapathirama Raghu

(57) ABSTRACT

A method for producing sclareol by fermentation of cigar tobacco flower buds is provided, including: mixing cigar tobacco flower buds with deionized water, sterilizing and adding edible yeast, then fermenting at 25-30° C. and 100-300 rpm/min for 24-30 h. This method uses cigar tobacco flower buds as the sole raw material, without adding additional nutrients, and only ferments tobacco flower buds with edible yeast to synthesize sclareol. Meanwhile, this method has extremely high synthesis efficiency.

6 Claims, No Drawings

METHOD FOR PRODUCING SCLAREOL BY FERMENTATION OF CIGAR TOBACCO FLOWER BUDS

FIELD OF THE DISCLOSURE

The present disclosure provides a method of producing sclareol, said method comprising mixing yeast with cigar tobacco flower buds for fermentation.

BACKGROUND

Sclareol is a fragrant substance with a herbal and fruity aroma. Its aroma is strong and long-lasting. Sclareol is widely found in *Perilla*, cherry, mint, lavender and other plants. It is commonly used as ingredient in cosmetics and perfume and food flavoring materials, with high economic value. Sclareol is also a potential antitumor drug. In addition, sclareol is widely used as a fragrance enhancer in the tobacco industry, for example, the patent CN202110487494.0 discloses a method to increase the sweet aroma of cigarettes, containing the following components: clary sage oil (containing sclareol) 0.01-0.06%, phenethyl alcohol 0.04-0.14%, etc.

At present, sclareol is mainly extracted from *Perilla* plants using solvents. After removing the volatile oil of *Perilla* by steam distillation, the residue is recrystallized with solvents such as petroleum ether and alkanes to obtain sclareol. This method is limited by factors such as long *Perilla* plants planting cycle, place of origin, environment, and climate. Moreover, the content of sclareol in *Perilla* plants is relatively low, only 15 kg of sclareol can be obtained from 1000 kg of hay, which is difficult to meet industrial needs. This method still faces issues such as complex processes and environmental pollution.

Firmenich company (M Schalk, L Pastore, M A Mirata et al. J. Am. Chem. Soc., 2012, 134:18900-18903)) uses geranylgeranyl pyrophosphate (GGPP) as raw material, which is catalyzed by SsLPPS to generate LPP, and then uses SsTPS to catalyze the production of sclareol (path a). KAO company (Hayase, K Igarashi. JP:2009060799, 1999) has developed a method for synthesizing ambroxide (path b). This method uses farnesol as the raw material and uses squalene-hopene cyclase and peptides with cyclase activity to prepare ambroxide. However, both methods mentioned above have problems such as long synthesis routes, high raw material costs, complex technical processes, and low yields.

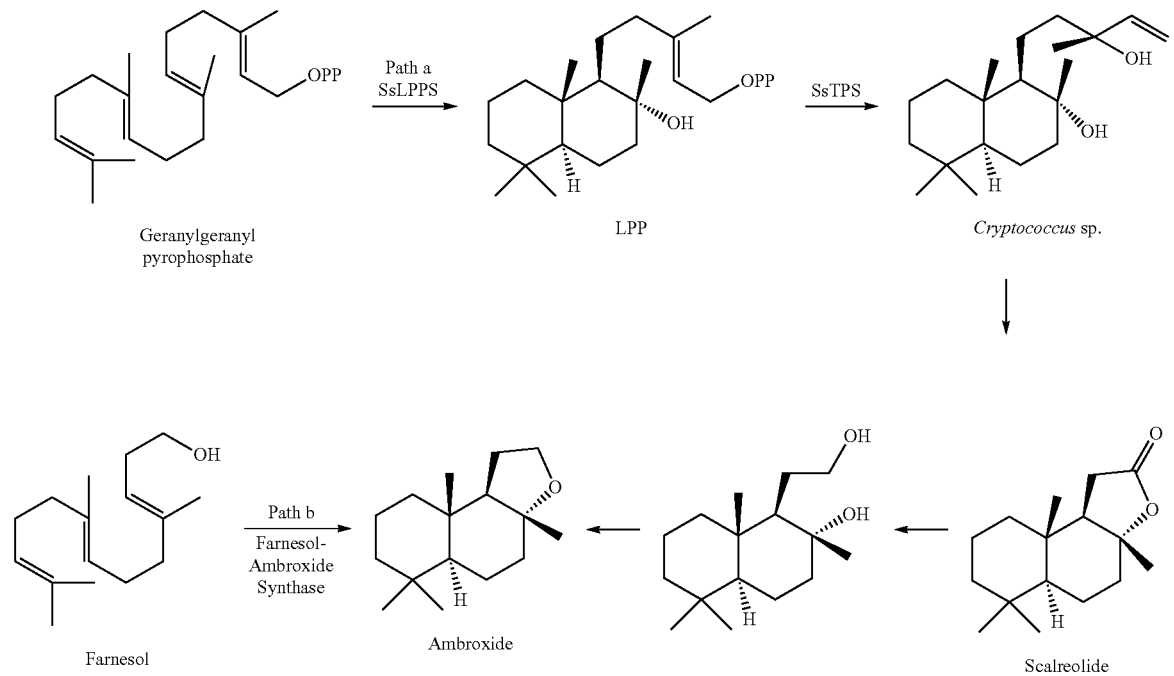

Document 1 (Yang W, Zhou Y J, et al. Engineering *Saccharomyces cerevisiae* for sclareol production. Chin J Biotech, 2013, 29(8):1185-1192.) constructs the *Saccharomyces cerevisiae* S6, which expresses labdenediol diphosphate synthase and terpene synthase. Strain S6 was fermented under shake flask culture conditions (2% glucose, 2% peptone and 1% yeast extract), and the yield of sclareol reached 8.9 mg/L. Document 2 (Song Y H, Shen H W, et al. High cell density culture of an engineered yeast strain for sclareol production. Chin J Biotech, 2015, 31(1):147-151.) constructs a *Saccharomyces cerevisiae* S7. Strain S7 was fermented under shake flask culture conditions (glucose15 g/L, $(NH_4)_2O_4$ 15 g/L, $KH_2PO_4$ 8 g/L, $MgSO_4 \cdot 7H_2O$ 6.2 g/L, etc., adjusting pH with pH 5.0 buffer) for 96 hours with a production of 15.2 mg/L of sclareol. Document 3 (Zhang X. Engineering *Saccharomyces cerevisiae* for production of limonene and sclareol. Tianjin University, 2021) constructs a *Saccharomyces cerevisiae* DEZ04. Strain DEZ04 was fermented in YPD medium (2% glucose, 2% peptone and 1% yeast extract), and added riboflavin at the beginning of fermentation. After 48 hours of fermentation, the yield of sclareol reached 36.45 mg/L, and after optimizing the conditions, the yield of sclareol reached 51.97 mg/L after 60 hours of fermentation. However, the yield of sclareol obtained by the above methods is relatively low.

Tobacco is an important economic crop. In order to improve the quality of tobacco leaves, the flower buds are usually removed during the flowering period to save plant nutrients for the growth and development of tobacco leaves. However, the removed flower buds have not been effectively applied. Document 4 (Xu CP, Meng DD, et al. Optimization of fermentation treatment condition of tobacco bud and preparation of tobacco flavor, Hubei Agricultural Sciences, 2018, 57(1):100-103) uses a yeast to ferment tobacco flower buds (Yunyan87), and the fermentation products were then subjected to the Maillard reaction. Through distillation extraction and GC-MS analysis, 63 aroma substances were detected, including palmitic acid, myristic acid, palmitic acid, benzyl alcohol, and phenylethanol. This document reports on the positive role of maillard reaction in yeast fermentation of tobacco flower buds for the preparation of tobacco flavor. However, the document did not detect sclareol, indicating that Yunyan87 does not have the conditions to produce sclareol after yeast fermentation and maillard reaction. At present, there are no reports on the production of sclareol through fermentation using tobacco flower buds in existing technologies.

As indicated above, providing a method for producing sclareol using tobacco flower buds is of great significance.

SUMMARY

The present disclosure provides a method for producing sclareol through fermentation of cigar tobacco flower buds. This method uses natural cigar tobacco flower buds as the sole raw material, and only undergoes yeast fermentation to efficiently prepare sclareol. This method has the advantages of simple process, low cost, easy control, and high yield.

The purpose of the disclosure is realized through the following technical solutions.

A method for producing sclareol by fermentation of cigar tobacco flower buds comprises the follows: cigar tobacco flower buds was mixed with deionized water, and the edible yeast was added after sterilization, and then fermented at 25-35° C. and 100-300 rpm/min for 24-30 h.

The inventor found that compared to culture medium containing nutrients such as protein and glucose, culture medium using cigar tobacco flower buds as the sole raw material can more efficiently promote the synthesis of sclareol.

In the fermentation system of the present disclosure, cigar tobacco flower buds are used as the sole raw material without adding additional nutrients (such as peptone, glucose, etc.), and edible yeast is used as the ferment, which can produce sclareol in a green and efficient manner.

Preferably, the cigar tobacco flower buds include at least one of the Chuxue CX10 flower buds, Chuxue CX14 flower buds, and Chuxue CX16 flower buds. For example, in some embodiments, the cigar tobacco flower buds are composed of the Chuxue CX10 flower buds, Chuxue CX14 flower buds, and Chuxue CX16 flower buds in a mass ratio of 1:1:1.

Preferably, the cigar tobacco flower buds are treated as follows: cleaning, drying, grinding the cigar tobacco flower buds, and passing the resulting powder through 40-80 mesh sieve to obtain the final flower bud powder.

Preferably, the mass ratio of the flower bud powder to deionized water is (1-15): 100. Moreover, it is more optimal when the mass ratio of the flower bud powder to deionized water is (4-8):100. More preferably, the mass ratio of the flower bud powder to deionized water is 6:100.

Preferably, the amount of added edible yeast is 0.5% to 3%. More preferably, the amount of added edible yeast is 1.5%.

Preferably, a fermenting process is performed at 30° C. and 200 rpm/min for 24 hours.

Preferably, the method for producing sclareol comprises the following steps:
S1: Cleaning, drying, grinding the cigar tobacco flower buds, and passing the resulting powder through 40-80 mesh sieve to obtain the final flower bud powder; and mixing the flower bud powder with deionized water in a mass ratio of (1-15):100, sterilizing at 110-130° C. for 15-20 minutes to obtain culture medium;
S2: Adding edible yeast of 0.5%-3% to the culture medium, and then fermenting for 24-30 h at 25-35° C. and 100-300 rpm/min to obtain the sclareol.

The above method for producing sclareol can also comprise: after fermentation, extracting sclareol from the fermentation broth by simultaneous distillation extraction (SDE), and analyzing its content by GC-MS.

The advantages of the technical scheme proposed in the disclosure are as follows.

(1) The present invention uses cigar tobacco flower buds as the sole raw material, without adding additional nutrients, and only ferments tobacco flower buds with edible yeast to efficiently synthesize sclareol. For example, in one embodiment, a fermentation broth with a content of 175 mg/L sclareol can be obtained after 24 hours of fermentation.

(2) The method for producing sclareol provided by the present invention has the characteristics of simple operation, low cost, high controllability, and high yield.

(3) The present invention provides a new approach for the resource utilization of cigar tobacco flower buds, which is of great significance for the recycling of tobacco resources.

DETAILED DESCRIPTION OF PREFERRED EMBODIMENTS

The invention will be further described in detail in combination with embodiments to make the purpose, technical scheme, and advantages of the invention clear. The specific embodiments described herein are only used to explain the invention and are not intended to limit the invention.

In an embodiment, a method for producing sclareol using cigar tobacco flower buds includes the following steps:
S1: Cleaning, drying, grinding the cigar tobacco flower buds, and passing the resulting powder through 40-80 mesh sieve to obtain the final flower bud powder; and mixing the flower bud powder with deionized water in a mass ratio of (1-15):100, sterilizing at 110-130° C. for 15-20 minutes to obtain culture medium;
S2: Adding edible yeast of 0.5%-3% to the culture medium, and then fermenting for 24-30 h at 25-35° C. and 100-300 rpm/min to obtain the sclareol.

The edible yeast used in the following examples and comparative examples is a commercially available yeast powder, such as high-activity dry yeast produced by Angel Yeast Co., Ltd. The cigar tobacco flower buds are composed of Chuxue CX10 flower buds, Chuxue CX14 flower buds and Chuxue CX16 flower buds in a mass ratio of 1:1:1.

The following embodiments are only illustrative examples of the specific implementation of the invention. The described embodiments are only a part of the embodiments of the invention, but the following embodiments should not be understood to limit the scope of protection claimed in the invention claims to any extent.

Example 1

This embodiment provides a method for producing sclareol through fermentation of cigar tobacco flower buds, comprising the following steps.

S1, Wash and dry the cigar tobacco flower buds, then crush them with a grinder and pass them through a 60 mesh sieve to obtain flower bud powder; mix the flower bud powder with deionized water in a mass ratio of 6:100 and divide into 250 mL culture flasks (100 mL per flask). Then sterilize at 121° C. for 20 minutes to obtain the culture medium.

S2, Add edible yeast (inoculation amount of 1.5%) to the culture medium obtained in step S1, and then ferment at 30° C. and 200 rpm/min for 24 hours.

S3, Extract sclareol from the fermentation broth obtained in step S2 by SDE, as follows:

Take 100 mL of fermentation broth and place it in a 1000 mL round-bottom flask, then add NaCl to form saturated brine. Meanwhile, take 60 mL of dichloromethane and place it in another 100 mL round-bottom flask. Connect the two round-bottom flasks to both sides of the SDE device. Round-bottom flask containing dichloromethane are heated in a 55° C. water bath, while round-bottom flask containing fermentation broth are heated in a 160° C. oil bath. When there is liquid reflux from the extraction tube to the flasks on both sides, start timing. After 2 hours, collect the extraction liquid, add anhydrous sodium sulfate, and use a rotary evaporator to vacuum concentration to obtain a concentrated solution (1-2 mL).

S4, After filtering the concentrated solution, determine the content of sclareol using GC-MS.

The GC-MS determination conditions are as follows:

Chromatographic column: HP-5MS capillary column (30 m×0.25 mm, 0.25 m). Temperature rise program for chromatographic column: maintaining at 40° C. for 2 minutes, then increasing to 200° C. at a rate of 2° C./min, maintaining for 5 minutes, and then increasing to 280° C. at a rate of 10° C./min. Column flow (He):1 mL/min. Sample size: 1 μL. Split ratio, 10:1. EI source. Electronic energy: 70 eV. Transfer line temperature: 250° C. Ion source temperature: 230° C. Mass scan range (m/z): 35-550. Identify the peaks of the target compound based on the National Institute of Standards and Technology database (NIST14).

According to the method described in this embodiment, after 24 hours of fermentation, SDE and GC-MS detection showed that the content of sclareol in the fermentation broth was 175 mg/L. This yield is 19.7 times that of document 1, 11.54 times that of document 2, and 3.37 times that of document 3. The synthesis efficiency of this embodiment is 7.29 mg/L h, which is 46.1 times that of document 2 and 8.42 times that of document 3.

Example 2

The method of this embodiment is basically the same as that of example 1, except that the fermentation time in step S2 is 30 hours.

According to the method described in this embodiment, after 30 hours of fermentation, SDE and GC-MS detection showed that the content of sclareol in the fermentation broth was 143 mg/L. This yield is 16 times that of document 1, 9.4 times that of document 2, and 2.75 times that of document 3. The synthesis efficiency of this embodiment is 4.77 mg/L h, which is 30.2 times that of document 2 and 5.51 times that of document 3.

Example 3

The method of this embodiment is basically the same as that of example 1, except that the mass ratio of flower bud powder to deionized water in step S1 is 8:100.

According to the method described in this embodiment, after 24 hours of fermentation, SDE and GC-MS detection showed that the content of sclareol in the fermentation broth was 107 mg/L.

Example 4

The method of this embodiment is basically the same as that of example 1, except that the mass ratio of flower bud powder to deionized water in step S1 is 2:100.

According to the method described in this embodiment, after 24 hours of fermentation, SDE and GC-MS detection showed that the content of sclareol in the fermentation broth was 14.1 mg/L.

Comparing example 1 and example 2, it was found that after the fermentation time changed from 24 hours to 30 hours, the yield of sclareol decreased from 175 mg/L to 143 mg/L. This indicates that as fermentation time prolongs, when the nutrients in the culture medium are insufficient to maintain cell growth or activity, the synthesized sclareol can be reused by cells as a nutrient, leading to a decreasing trend in content.

Comparing example 1, example 3, and example 4, it was found that the mass ratio of flower bud powder to deionized water will affect the growth and metabolism of edible yeast, thereby affecting the synthesis efficiency of sclareol.

Comparative Example 1

The method of this comparative example is basically the same as example 1, except that the culture medium in step S1 is a mixture of flower bud powder and YEP medium (containing 2% peptone, 2% glucose, and 1% yeast extract) in a mass ratio of 8:100.

According to the method described in this comparative example, after 24 hours of fermentation, SDE and GC-MS detection showed that the content of sclareol in the fermentation broth was 57 mg/L.

Comparative Example 2

The method of this comparative example is basically the same as example 1, except that the culture medium in step S1 is a mixture of flower bud powder and YEP medium (containing 2% peptone, 2% glucose, and 1% yeast extract) in a mass ratio of 10:100.

According to the method described in this comparative example, after 24 hours of fermentation, SDE and GC-MS detection showed that the content of sclareol in the fermentation broth was 37 mg/L.

Comparing example 3 with comparative example 1 and 2, it was found that nutrient rich medium (tobacco bud powder+YPE medium) could not improve the synthesis efficiency of sclareol, and even reduced the yield of sclareol. The reason is that YPE medium is a commonly used and efficient medium for promoting yeast growth, and there is a competitive relationship between yeast growth and the synthesis of sclareol. Therefore, it is necessary to control the total amount of nutrients in the culture medium within a certain range. It can be understood that the above nutrients include precursor substances used for the synthesis of sclareol, which come from cigar tobacco flower buds. When using nutrient rich medium to cultivate yeast, the precursor substances are consumed for cell growth, resulting in a decrease in the yield of sclareol. Therefore, it is necessary to control the growth efficiency and total cell quantity of yeast reasonably during fermentation. The present invention only uses cigar tobacco flower buds and deionized water to make a culture medium, which contains nutrients that can meet the growth needs of yeast and also meet the conversion of precursor substances in flower buds into sclareol, enabling efficient synthesis of sclareol. As mentioned above, the culture medium of the present invention is the most distinct from the prior art (such as documents 1, 2, and 3).

Comparative Example 3

This comparative example provides a method for producing sclareol, comprising the following steps.

S1, Divide YPE medium (containing 2% peptone, 2% glucose, and 1% yeast extract) into 250 mL culture flasks (100 mL per flask), and then sterilize at 121° C. for 20 minutes.

S2, Add edible yeast (inoculation amount of 1.5%) to the medium obtained in step S1 and then ferment at 30° C. and 200 rpm/min for 24 hours.

S3, Same as step S3 in example 1.

S4, Same as step S4 in example 1.

According to the method described in this comparative example, no sclareol was detected in the fermentation broth through SDE and GC-MS detection.

This comparative example indicates that yeast does not have the ability to synthesize sclareol in YEP medium, and also implies that the nutritional components contained in cigar tobacco flower buds are precursor conditions for utilizing yeast to synthesize sclareol.

Comparative Example 4

The method of this comparative example is basically the same as example 1, except that the cigar tobacco flower buds in step S1 are replaced with flue cured tobacco (Yunyan87) flower buds.

According to the method described in this comparative example, no sclareol was detected in the fermentation broth through SDE and GC-MS detection. This indicates that the types and sources of tobacco flower buds are the basis and precursor conditions for the synthesis of sclareol.

The above descriptions are only preferred embodiments of the present invention and are not intended to limit the present invention. Any modification, equivalent replacement, improvement, etc., made within the spirit and principle of the present invention shall be included in the protection of the present invention.

What is claimed is:

1. A method for producing sclareol by fermentation of cigar tobacco flower buds, comprising:
   mixing the cigar tobacco flower buds with deionized water in a mass ratio of (1-15):100, sterilizing, adding edible yeast, then fermenting at 25-30° C. and 100-300 revolutions per minute (rpm/min) for 24-30 hours (h);
   wherein the cigar tobacco flower buds are a bud mixture of Chuxue CX10 flower buds, Chuxue CX14 flower buds, and Chuxue CX16 flower buds in a mass ratio of 1:1:1; and
   wherein an inoculation amount of the edible yeast added is 0.5%-3%.

2. The method for producing the sclareol by the fermentation of the cigar tobacco flower buds according to claim 1, wherein the cigar tobacco flower buds are treated as following:
   cleaning, drying, grinding the cigar tobacco flower buds, and passing resulting powder through 40-80 mesh sieve to obtain flower bud powder.

3. The method for producing the sclareol by the fermentation of the cigar tobacco flower buds according to claim 1, wherein the fermentation is performed at 30° C., 200 rpm/min for 24 h.

4. The method for producing the sclareol by the fermentation of the cigar tobacco flower buds according to claim 1, specifically comprising following steps:
   (1) cleaning, drying, grinding the cigar tobacco flower buds to obtain resulting powder, and passing the resulting powder through 40-80 mesh sieve to obtain flower bud powder; mixing the flower bud powder with the deionized water in the mass ratio of (1-15):100 to obtain a mixture, sterilizing the mixture at 110-130° C. for 15-20 minutes to obtain a culture medium;
   (2) adding the edible yeast to the culture medium at an amount of 0.5%-3%, and then fermenting the culture medium added with the edible yeast for 24-30 h at 25-35° C. and 100-300 rpm/min, so as to obtain a fermentation broth.

5. The method for producing the sclareol by the fermentation of the cigar tobacco flower buds according to claim 4, further comprising step (3): after the fermentation, extracting the sclareol from the fermentation broth by simultaneous distillation extraction (SDE), and analyzing content of the sclareol by gas chromatography-mass spectrometry (GC-MS).

6. A method for producing sclareol by fermentation of cigar tobacco flower buds, comprising:
   mixing Chuxue CX10 flower buds, Chuxue CX14 flower buds, and Chuxue CX16 flower buds in a mass ratio of 1:1:1 to obtain the cigar tobacco flower buds;
   cleaning, drying, grinding the cigar tobacco flower buds to obtain resulting powder, and passing the resulting powder through 40-80 mesh sieve to obtain flower bud powder;
   mixing the flower bud powder with deionized water in a mass ratio of (1-15):100 to obtain a mixture, and sterilizing the mixture at 110-130° C. for 15-20 minutes to obtain a culture medium; and
   adding edible yeast to the culture medium at an inoculation amount of 0.5%-3%, and then fermenting the culture medium added with the edible yeast for 24-30 h at 25-35° C. and 100-300 rpm/min, to thereby obtain a fermentation broth;
   wherein in the method for producing sclareol, neither peptone nor glucose is added.

* * * * *